United States Patent
Schutte et al.

[11] Patent Number: 5,100,391
[45] Date of Patent: * Mar. 31, 1992

[54] DOUBLE-BLADED SCALPEL

[76] Inventors: Michael J. Schutte; Jerry J. King, both of 2825 Fort Missoula Rd., both of Missoula, Mont. 59801

[*] Notice: The portion of the term of this patent subsequent to Jun. 25, 2008 has been disclaimed.

[21] Appl. No.: 679,646

[22] Filed: Apr. 2, 1991

Related U.S. Application Data

[63] Continuation-in-part of Ser. No. 503,706, Apr. 3, 1990, Pat. No. 5,026,385.

[51] Int. Cl.⁵ .............................................. A61B 17/32
[52] U.S. Cl. ...................................... 606/167; 30/304
[58] Field of Search ............... 606/167, 170, 160, 183, 606/166; 30/121, 131, 113.1, 173, 304

[56] References Cited
U.S. PATENT DOCUMENTS

| | | | |
|---|---|---|---|
| 479,102 | 7/1892 | Willbrandt | 30/343 |
| 3,452,754 | 8/1986 | Stayer | 606/167 |
| 3,998,229 | 12/1976 | Barton | 606/167 |
| 4,578,865 | 4/1986 | Keller | 30/304 |
| 4,688,570 | 8/1987 | Kramer et al. | 606/166 |
| 5,026,385 | 6/1991 | Schutte et al. | 606/167 |

FOREIGN PATENT DOCUMENTS 2637172 2/1978 Fed. Rep. of Germany ........ 30/343

Primary Examiner—C. Fred Rosenbaum
Assistant Examiner—William Lewis
Attorney, Agent, or Firm—Wells, St. John & Roberts

[57] ABSTRACT

A double-bladed scalpel for removal of tissues requiring consistent width along their length. Identical metal scalpel blades are mounted to an integral rigid supporting handle. The two blades protrude outwardly from one bifurcated handle end. A contoured finger rest permits the user to exert substantial cutting pressure when using the scalpel in applications where scribing of bony tissue is required.

11 Claims, 3 Drawing Sheets

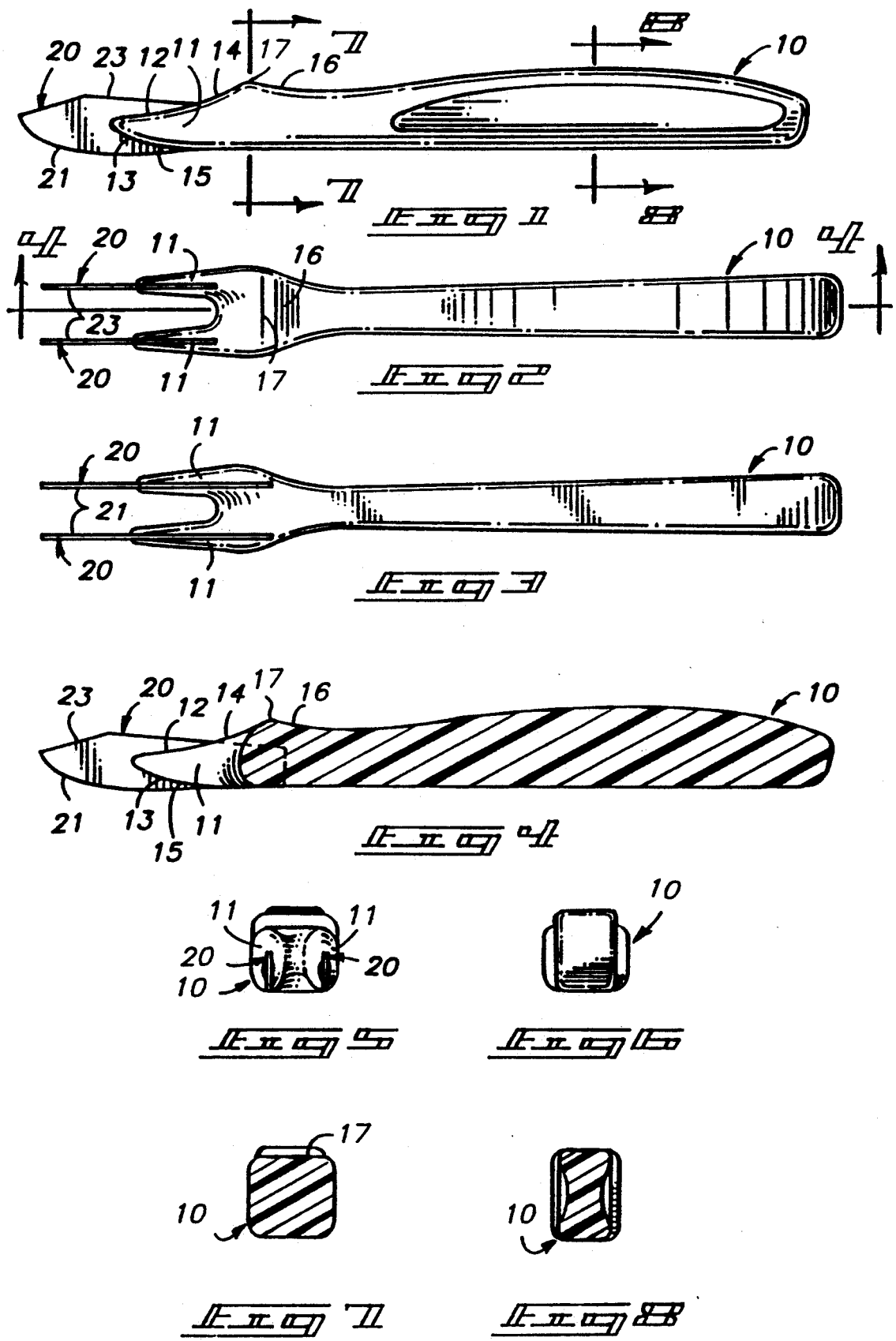

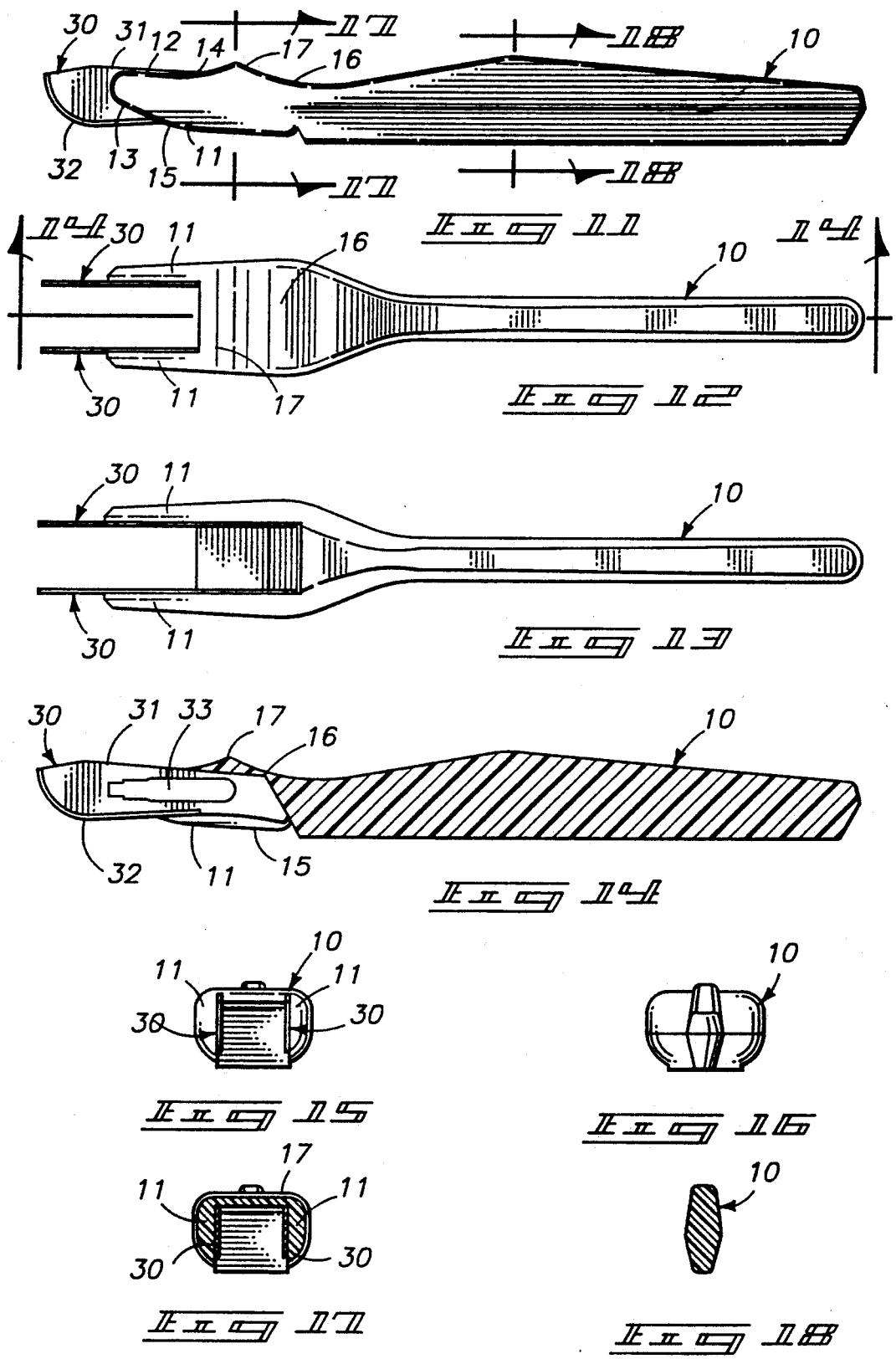

DOUBLE-BLADED SCALPEL

RELATED APPLICATION

This application is a continuation-in-part of pending U.S. Pat. application Ser. No. 503,706, filed on Apr. 3, 1990, now U.S. Pat. No. 5,026,385 titled "Double-Bladed Scalpel."

TECHNICAL FIELD

The technical field of this invention pertains to surgical scalpels.

BACKGROUND OF THE INVENTION

The present scalpel was designed specifically for use in reconstruction of the anterior cruciate ligament in the knee. In this procedure, a strip of patellar tendon measuring between 10 to 12 millimeters in width is harvested from the middle of the tendon. The strip of tissue must be consistent in width to provide maximum strength in the resulting graft.

Current techniques for harvesting such strips of tissue require making two separate incisions in sucession, the second incision being guided by manually holding a ruler parallel to the first. This typically results in a graft that varies in width along its length. The differences in width from one point to another along the graft can range up to three millimeters.

When making sequential incisions along a tendon such as this, the tension within the tendon is modified after production of the first incision. The changes in tension affect the consistency of the second incision in a pattern that cannot be predetermined. It was recognized that if one could simultaneously produce the two incisions along opposite sides of the tendon, the tension encountered within the tendon would then be constant and not affect the width of the resulting strip.

The initial efforts to produce two parallel incisions that led to this development were accomplished by attempting to attach two conventional scalpels to one another in spaced parallel positions. While this constituted an improvement over the production of separate incisions, undersirable deviations in graft width continued to be encountered. Such variations in width are particularly difficult to prevent in the above-described surgical procedure, where the strip of patellar tendon is harvested along the middle of its underlying bone. The bony surfaces are curved and tend to splay two surgical blades outwardly from one another in response to the cutting pressures necessary to scribe the bone.

The present invention was developed in an effort to rigidly support two surgical blades for such procedures. It assures that sufficient pressure can be simultaneously applied to them to scribe underlying bone when this is required.

BRIEF DESCRIPTION OF THE DRAWINGS

The preferred embodiment of the invention is illustrated in the accompanying drawings, in which:

FIG. 1 is a side view of a scalpel;
FIG. 2 is a top view;
FIG. 3 is a bottom view;
FIG. 4 is a longitudinal sectional view taken along line 4—4 in FIG. 2;
FIG. 5 is a left hand end view;
FIG. 6 is a right hand end view;
FIG. 7 is a cross-sectional view taken along line 7—7 in FIG. 1;
FIG. 8 is a sectional view taken along line 8—8 in FIG. 1;
FIG. 11 is a side view of a second embodiment;
FIG. 12 is a top view;
FIG. 13 is a bottom view;
FIG. 14 is a longitudinal sectional view taken along line 14—14 in FIG. 2;
FIG. 15 is a left hand end view;
FIG. 16 is a right hand end view;
FIG. 17 is a cross-sectional view taken along line 17—17 in FIG. 11;
and
FIG. 18 is a sectional view taken along line 18—18 in FIG. 11.

PREFERRED EMBODIMENTS

Figure 9:
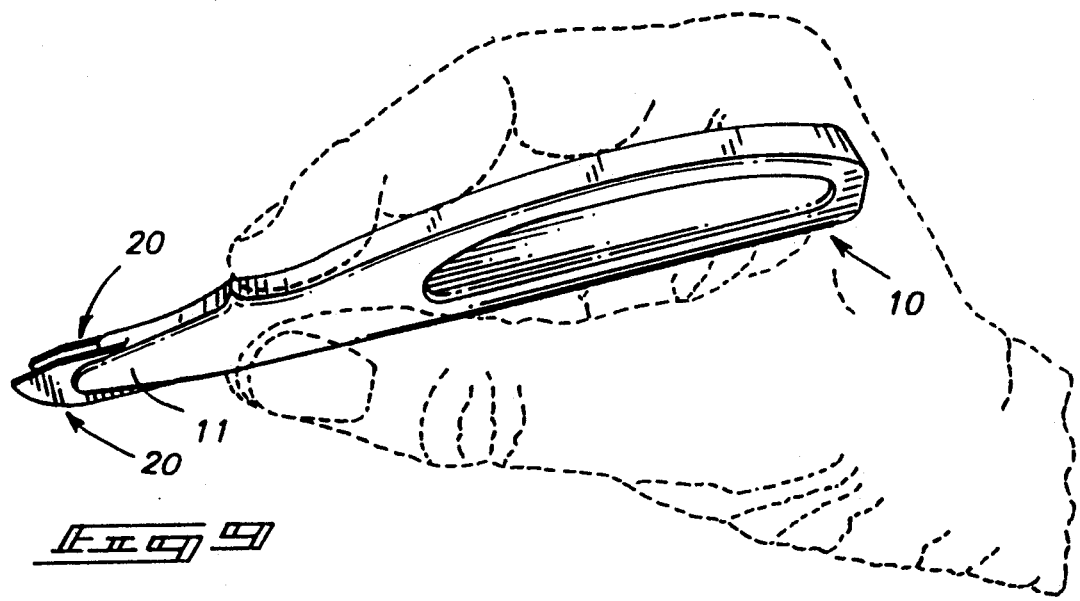
FIG. 9 is a diagrammatic side view showing the manner by which the scalpel is gripped by a user.

The following disclosure of the invention is submitted in furtherance with the constitutional purpose of the Patent Laws "to promote the progress of science and useful arts" (Article 1, Section 8).

FIGS. 1-8 illustrate features of a first embodiment of a double-bladed scalpel according to this disclosure. It was designed specifically for harvesting a strip of patellar tendon during reconstruction of the anterior cruciate ligament in the knee. This surgical procedure is well known and further details concerning the application of such grafts is not believed to be necessary to an understanding of the present invention.

The scalpel comprises an elongated handle 10 formed integrally of solid rigid material. It is preferably molded from rigid plastic resins, but can be fabricated of metal or other suitable rigid materials where a more durable or reusable scalpel construction is desired.

The scalpel is provided with a pair of identical elongated surgical cutting blades 20. Each blade has a sharpened lower edge 21 that extends to an outer blade end. The lower edge 21 of each blade is substantially flush with the bottom surface 13 of handle 10 to present a scalpel having a sharpened lower edge 21 that smoothly merges into the bottom surface 13 along the handle 10.

Each blade 20 also includes an upper edge extending along its length from the inner end attached to handle 10 to its outer end, where it joins the sharpened lower edge 21. The upper edge 23 of each blade 20 is embedded within the handle structure and is spaced from the upper surface 12 of handle 10 (see FIG. 1).

The blades each also include an inner blade end 22. The inner blade ends 22 are individually fixed to the handle 10 in parallel side by side positions protruding outwardly from one handle end. The blades are preferably mounted in the handle in a permanent manner, but can be replaceably mounted if desired.

The one end of the elongated handle 10 that mounts the two blades 20 is bifurcated to present two rigid spaced extensions 11. Each extension 11 has upper and lower surfaces 14 and 15, respectively. They individually mount the two blades 20 with the upper surface 14 of each extension covering the upper edge 23 of the blade 20 mounted within it. The lower surface 15 of each extension recedes upwardly and outwardly from the lower edge 21 of the blade 20 (see FIG. 1).

The inner end 22 of each blade 20 is substantially overlapped by its supporting extension 11. As can be seen in the drawings, approximately one-half of the longitudinal length of each blade 20 is overlapped by the elongated handle 10. The resulting longitudinal overlap between the rigid extensions 11 of handle 10 and each blade 20 mounted within it serves to prevent outward splaying of the protruding blade portions.

When applying the present invention to a single-use scalpel, each blade 20 is permanently enbedded within the elongated handle 10. This can be accomplished either by molding the handle structure about the metal blades or by molding blade slots within the handle extensions 11 and assembling the scalpel by subsequently inserting the blades 20 after molding of the handle 10. Such fabrication requires the production of a permanent connection between the handle 10 and each blade 20. This can be accomplished by use of a suitable adhesive compatible with the involved respective materials.

In order to facilitate scribing of underlying bone as a strip of tendon is being cut, it is desirable that substantial finger pressure be directed to the two blades 20. This is accomplished by shaping the handle 10 to present an exterior sufaced that fits the hand of a user when grasped in a pencil-like grip during harvesting of a strip of tissue requiring parallel edges. The manner by which the handle 10 is grasped is illustrated in FIGS. 8 and 9.

The handle 10 presents the user with a relatively thick and substantial structure in comparison to the usual thin handle of a conventional scalpel. It is contoured to provide a comfortable fit in the hand of a user. Its cross-sectional shape is in the form of a thickened rectangle. The thickened rectangular shape of the handle assists in preventing twisting within the hands of a user.

Figure 10:
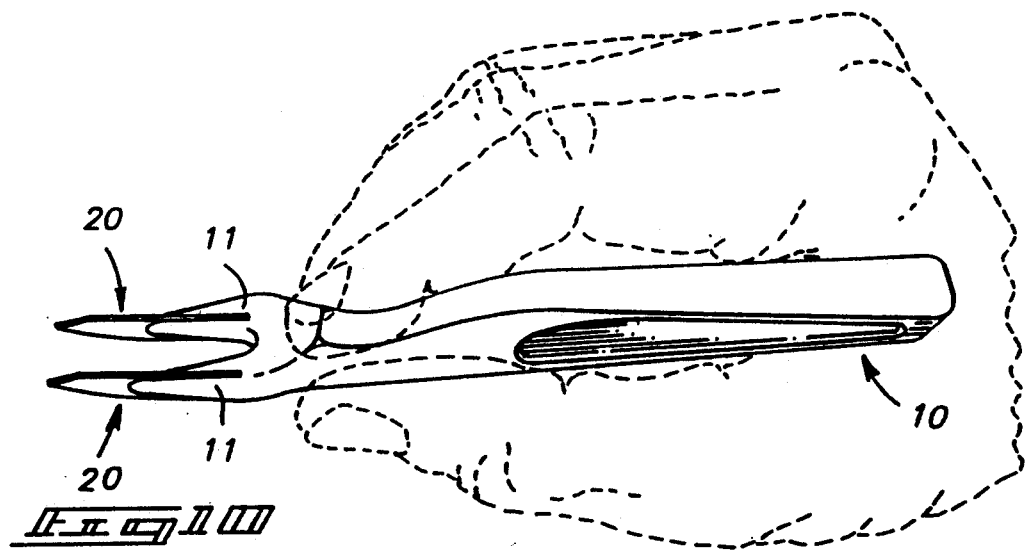
FIG. 10 is a similar diagrammatic top view.

Handle 10 includes a contoured finger rest 16 extending across its upper surface 12 at a location inwardly adjacent to the one end of handle 10 that mounts the two blades 20. The finger rest 16 is defined by a transverse ridge 17 extending across the full width of the handle 10. The ridge 17 provides an abutment for the index finger of a user (See FIGS. 9 and 10). This allows substantial downward pressure to be exerted by the end of the finger to urge the blades 20 into the tissue being cut. To assure that this finger pressure is applied directly to the blades 20, it is preferable that the inner ends of blades 20 be located within the handle 10 at a longitudinal position under the finger rest 16. (See FIGS. 1 and 2).

FIGS. 11–18 show a modification of the scalpel. Those elements of the scalpel that correspond to elements described above with respect to the first embodiment are denoted by the same reference numerals as previously used. In the second embodiment, the inner ends of two conventional scalpel blades 30 having upper edges 31 and cutting edges 32 are attached alongside planar parallel surfaces of two rigid spaced extensions by projections 33 formed integrally with the extensions 11. The projections 33 can be heated and compressed to form outer enlargements that secure blades 30 permanently on the resin handle.

As in the first embodiment, the extensions 11 have lengths less than the lengths of the blades 30. They substantially overlap and individually support the blades 30 to prevent splaying of the outwardly protruding blade portions. The finger rest adjacent to the bifurcated parallel side-by-side extensions enables the user to apply substantial downward pressure on the extensions 11 and blades 30.

The above scalpel construction provides an extremely rigid construction for supporting the parallel cutting blades 20 and 30. The support for the blades is adequate to prevent them from splaying while scribing the underlying bone beneath a tendon, where considerable force is often exerted between the hand of the user and the bone.

The present construction also readily lends itself to production from disposable plastic resins, such as polycarbonate. Designing a disposable scalpel for single-use purposes helps to prevent any potential spread of infectious disease that might occur by reusing the product. However, the invention is not to be limited to any particular materials, and can be applied to more permanent metal structures that can be sterilized between uses. While permanent mounting of the two blades is preferred, one can provide a releasable mounting arrangement where blade replacement is desired.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims appropriately interpreted in accordance with the doctrine of equivalents.

We claim:

1. A double bladed scalpel, comprising:
   a rigid handle;
   a pair of cutting blades outwardly protruding from one end of the handle in transversely-spaced parallel side-by-side positions across the handle, each blade having a sharpened lower edge extending to an outer blade end;
   the blades each having an inner blade end, the inner blade ends of the two blades being mounted to the one end of the handle;
   the one end of the elongated handle being bifurcated into two integral rigid extensions arranged in transversely-spaced parallel side-by-side positions across the one end of the handle, each extension overlapping and individually supporting one of the blades to prevent splaying of the outwardly protruding blade portions.

2. The double-bladed scalpel of claim 1, wherein the handle is made of plastic resin material.

3. The double-bladed scalpel of claim 1, wherein the handle is made of metal.

4. The double-bladed scalpel of claim 1, wherein the blades are permanently fixed to the handle.

5. The double-bladed scapel of claim 1, wherein the blades are releasably mounted to the handle.

6. The double-bladed scalpel of claim 1, wherein each extension overlaps a single side of a blade.

7. A double-bladed scalpel, comprising:
   a rigid elongated handle;
   a pair of identical elongated cutting blades, each blade having a sharpened lower edge extending to an outer blade end;
   the blades each having an inner blade end, the inner blade ends of the two blades being mounted to one end of the handle in parallel side-by-side positions protruding outwardly from the one handle end;
   the one end of the elongated handle being bifurcated into two integral rigid extensions, each extension individually supporting one of the blades;
   the elongated handle including a contoured finger rest formed across its upper surface, the finger rest terminating in a transverse ridge extending across the full width of the handle at a location inwardly adjacent to its one end; and the inner ends of the blades being located at a longitudinal position under the finger rest.

8. A double bladed scalpel, comprising:

a rigid elongated handle, the handle having an exterior cross-sectional shape in the form of a thickened rectangle to fit a user's hand when grasped in a pencil-like grip and to assist in preventing twisting of the handle within the hands of a user during harvesting of a strip of tissue requiring parallel edges;

a pair of identical elongated cutting blades outwardly protruding from one end of the handle in transversely-spaced parallel side-by-side positions across the handle, each blade having an elongated upper edge and an elongated lower edge, the lower edge of each blade being sharpened and extending to an outer blade end at which it meets the upper edge;

the blades each having an inner blade end, the inner blade ends being mounted to the one end of the handle;

the one end of the elongated handle being bifurcated into two integral rigid extensions having lengths less than the lengths of the blades and being arranged in transversely-spaced parallel side-by-side positions across the handle, each extension overlapping and individually supporting one of the blades to prevent splaying of the outwardly protruding blade portions.

9. A double-bladed scalpel, comprising:

a rigid elongated handle having an exterior cross-sectional shape in the form of a thickened rectangle to fit a user's hand when grasped in a pencil-like grip and to assist in preventing twisting of the handle within the hands of a user during harvesting of a strip of tissue requiring parallel edges;

a pair of identical cutting blades, each blade having an elongated upper edge and an elongated lower edge, the lower edge of each blade being sharpened and extending to an outer blade end at which it meets the upper edge;

the blades each having an inner blade end, the inner blade ends being mounted to one end of the handle in parallel side-by-side positions protruding longitudinally outward from the handle;

the one end of the elongated handle being bifurcated into two intergral rigid extensions, each extension individually supporting one of the blades;

the elongated handle including a contoured finger rest formed across its upper surface, the finger rest terminating in a transverse ridge extending across the full width of the handle at a location inwardly adjacent to its one end;

the inner ends of the blades being located under the finger rest.

10. A double bladed scalpel, comprising:

a contoured elongated handle formed integrally of rigid material, the handle having an exterior cross-sectional shape in the form of a thickened rectangle shaped to fit a user's hand when grasped in a pencil-like grip and to assist in preventing twisting of the handle within the hands of a user during harvesting of a strip of patellar tendon tissue and an adjacent strip of bone from the tibial tuberosity where consistency in width is required on the harvested tissue to assure maximum strength in the resulting graft;

a pair of identical metal cutting blades outwardly protruding from one end of the handle in transversely-spaced parallel side-by-side positions across the handle, each blade having an elongated upper edge and an elongated lower edge, the lower edge of each blade being sharpened and extending to an outer blade end at which it meets the upper edge;

the blades each having an inner blade end, the inner blade ends being mounted to the one end to the handle with portions of their respective lower edges protruding longitudinally outward from the one handle end, the inner end of each blade being substantially overlapped by the one handle end to prevent splaying of the protruding blade portions while scribing bony tissue underlying the harvested tendon;

the one end of the elongated handle being bifurcated into two integral rigid extensions having lengths less than the lengths of the blades and being arranged in transversely-spaced parllel side-by-side positions across the one end of the handle, each extension substantially overlapping and individually supporting one of the blades to prevent splaying of the outwardly protruding blade portions during harvesting of graft tissue in anterior cruciate ligament reconstructive surgery.

11. A double-bladed scalpel for the harvesting of graft tissue in anterior cruciate ligament reconstructive surgery, comprising:

contoured elongated handle formed integrally of rigid material, the handle having an exterior cross-sectional shape in the form of a thickened rectangle shaped to fit a user's hand when grasped in a pencil-like grip and to assist in preventing twisting of the handle within the hands of a user during harvesting of a strip of patellar tendon tissue and an adjacent strip of bone from the tibial turberosity requiring consistency in width for maximum strength in the resulting graft;

a pair of identical metal cutting blades, each blade having an elongated upper edge and an elongated lower edge, the lower edge of each blade being sharpened and extending to an outer blade end at which it meets the upper edge;

the blades each having an inner blade end, the inner blade ends being mounted to one end of the handle in parallel side-by-side positions with portions of their respective lower edges protruding longitudinally outward from the one handle end, the inner end of each blade being substantially overlapped by the one handle end to prevent splaying of the protruding blade portions while scribing bony tissue underlying the harvested tendon;

the one end of the elongated handle being bifurcated into two integral rigid extensions, each extension individually supporting one of the blades;

the elongated handle including a contoured finger rest formed across its upper surface, the finger rest terminating in a transverse ridge extending across the full width of the handle at a location inwardly adjacent to its one end;

the inner ends of the blades being located under the finger rest.

* * * * *